United States Patent [19]
Hill et al.

[11] Patent Number: 5,496,452
[45] Date of Patent: Mar. 5, 1996

[54] SUBSTRATE REGENERATING BIOSENSOR

[75] Inventors: Norman Hill, deceased, late of Dorset, England, by Judith A. Hill, executrix; Anthony E. G. Cass, London, England; Mark H. Smit, Honolulu, Hi.

[73] Assignee: The Secretary of State for Defence in Her Britannic Majesty's Government of the United Kingdom of Great Britain and Northern Ireland, London, England

[21] Appl. No.: 17,187

[22] Filed: Jan. 4, 1993

Related U.S. Application Data

[63] Continuation of PCT/GB91/00684, Apr. 30, 1991.

[30] Foreign Application Priority Data

May 1, 1990 [GB] United Kingdom .................. 9009761

[51] Int. Cl.[6] ........................ G01N 27/26; G01N 33/53; G01N 33/00
[52] U.S. Cl. ........................ 205/777.5; 435/7.1; 435/7.9; 435/7.92; 436/2; 436/109; 436/119; 205/780.5; 205/782
[58] Field of Search ..................... 204/403, 415, 204/418, 153.12, 153.14, 153.17, 153.19, 153.1; 435/288, 291, 817, 7.1, 7.9, 7.92; 436/2, 109, 119, 517, 532

[56] References Cited

U.S. PATENT DOCUMENTS

| | | | |
|---|---|---|---|
| 4,220,503 | 9/1980 | Johnson | 204/153.12 |
| 4,444,880 | 4/1984 | Tom | 435/7 |
| 5,149,630 | 9/1992 | Forrest et al. | 204/403 |
| 5,316,911 | 5/1994 | Baek et al. | 435/7.9 |
| 5,320,725 | 1/1994 | Gregg et al. | 204/153.12 |

OTHER PUBLICATIONS

Analytical Chemistry, vol. 62, Nov. 15, 1990 American Chemical Society Smit et al "Cyanide detection using a substrate . . . biosensor" pp. 2429–2436.

Analytical Chemistry, vol. 56, Apr. 1984 American Chemical Society Cass et al "Ferrocene–mediated enzyme electrode . . . glucose" pp. 667–671.

Biosensors & Bioelectronics. vol. 5, 1990 Elsevier Sccience Publishers Albery et al "Inhibited enzyme . . . and HCN" pp. 397–413.*

*Primary Examiner*—Bruce F. Bell
*Attorney, Agent, or Firm*—Nixon & Vanderhye

[57] ABSTRACT

A biosensor for the detection and determination of the concentration of toxins by use of enzyme inhibition. Inhibition biosensors are affected by non-specific denaturation and substrate utilization which both result in a limited operational lifetime. These problems are mitigated by providing in an environment an enzyme which is oxidized by hydrogen peroxide the oxidized enzyme being reduced by an electron transfer agent, such as ferrocene, which is itself oxidized in the process. The electron transfer agent is capable of regeneration back to the reduced state and the extend of electron transfer regeneration gives a measure of enzyme inhibition by toxin. Electro-chemical technique allows for the generation of hydrogen peroxide from oxygen in aqueous media and the reduction of oxidized electron transfer agent. Immobilization of the enzyme to an electrode increases efficiency while potentially reducing denaturation. The biosensor can be used for the environmental determination of toxins like cyanide.

17 Claims, 5 Drawing Sheets

SUBSTRATE REGENERATING BIOSENSOR

This application is a continuation of PCT/GB91/00684 filed on Apr. 30, 1991.

BACKGROUND OF THE INVENTION

The present invention relates to a detection technique and apparatus based on a substrate regenerating biosensor for use specifically but not exclusively for the sensing of cyanide. Various techniques have been devised for the detection of cyanide and determination of its concentration and these include sensitive colorimetric methods, electrochemical analysis and techniques requiring sophisticated instrumentation such as atomic absorption spectroscopy and computer assisted pattern recognition. However, there are certain inherent difficulties in the detection and determination of cyanide with many of the procedures requiring purification or volatilization of cyanide. Furthermore, most methods suffer from a lack of specificity and problems of interference. The application of physical techniques to a method of continuous monitoring is still being sought.

Biosensors for cyanide have been investigated based on cyanide's toxicity towards the biochemical activity of cytochrome oxidase. By binding to cytochrome oxidase, which is the terminal component in the electron transport chain of mitochondria, cyanide blocks an electron transfer and consequently stops electron flow in the respiratory chain.

By monitoring the electrochemical activity of cytochrome oxidase it is possible to detect the presence of toxic compounds such as cyanide, sulphide and azide from the inhibition of current. Inhibition sensors, such as those based on cytochrome oxidase operate under conditions of an enzyme limited signal rather than a transport limited one and these sensors are therefore sensitive to changes in enzyme activity.

Unfortunately inhibition sensors are susceptible to non-specific denaturation of the enzyme as well as the specific inhibitors resulting in the signal derived from the enzyme gradually decreasing even in the absence of inhibitor and limiting the operational lifetime. Furthermore substrate utilization eventually results in operational failure or the biosensor when the substrate is exhausted.

Consequently there is a need for a method for the detection and determination of concentration or toxins such as cyanide which overcomes or at least mitigates the disadvantages of the described techniques.

SUMMARY OF THE INVENTION

Accordingly there is provided a method for the detection and determination of concentration of a toxin which inhibits the electron transfer activity of an enzyme which comprises the steps of:

(a) providing in an environment an enzyme selected from peroxidase, catalase and oxygenase whose electron transfer activity is inhibited when bound to the toxin:

(b) providing hydrogen peroxide in the environment to oxidize the enzyme;

(c) reducing the oxidized enzyme with an electron transfer agent, the agent being oxidized in the process;

(d) detecting the presence and concentration of the inhibiting toxin by the change and extent to which the electron transfer agent is regenerated from its oxidized state.

As the ability of the electron transfer agent to be regenerated is dependent upon the enzyme's ability to oxidize the agent there is a proportional relationship between the two. In an enzyme limited system where the enzyme's electron transfer activity is depleted through inhibition by electro-active or electro-passive interferents the effect will be manifested in there being less oxidized electron transfer agent to regenerate back to its reduced state. Consequently this provides the basis for a detector for compounds which exhibit toxicity towards the electron transfer activity of the enzyme. Detection is achieved by noting a decrease in the level of regeneration of electron transfer agent while the degree to which regeneration is affected by enzyme inhibition provides an indication of the concentration of inhibitor present.

Preferably the enzyme is a peroxidase.

Preferably the environment is an aqueous environment so that the hydrogen peroxide is produced from oxygen dissolved in the aqueous environment, the hydrogen peroxide subsequently being reduced to water in raising the oxidation level of the enzyme. Alternatively the environment could be organic, etc., but it is in any case preferable that the environment is capable of providing enough protons and dissolved oxygen to produce the hydrogen peroxide rather than the hydrogen peroxide needing to be added from an external source. Preferably the reduction of oxygen to hydrogen peroxide takes place at a primary electrode and regeneration of the electron transfer agent takes place at a secondary electrode. The rate of generation of hydrogen peroxide at the primary electrode is controlled by the applied potential. The current at the secondary electrode which results from electron transfer agent regeneration is diagnostic of the catalytic state of the enzyme and hence the level of toxin inhibition.

Preferably the aqueous solution is able to absorb oxygen from either the atmosphere or some alternative source so that there is continuous generation of the substrate hydrogen peroxide by the primary electrode with the secondary electrode ensuring the regeneration of the electron transfer agent. Preferably the aqueous solution is well buffered if the oxygen source is atmospheric. This type of sensor may therefore be self-supporting and does not require constant maintenance and replenishment.

Because the catalytic activity of an enzyme is very specific to its substrate it can also be very sensitive to the presence of specific compounds which inhibit the enzyme's catalytic activity. Consequently the technique of the present invention can be made very specific in the detection of compounds and the enzyme used is chose with regard to the inhibitory effect a compound requiring detection will have upon the enzyme's activity. Furthermore compounds which exhibit high toxicity towards the enzyme will be more easily detected than those showing lower toxicity as the former will have a more profound effect upon enzyme activity and hence have a greater effect on regeneration of electron transfer agent.

It is intended that the biosensor will be used mainly for toxins in the gaseous phase. However the toxins could alternatively be in the liquid or solid phase provided that they can ultimately inhibit enzyme activity.

Conveniently the enzyme used is immobilized to provide better control over its catalytic activity and to increase the lifetime of the biosensor. Immobilization of the enzyme at the primary electrode can prevent protein fouling of the secondary electrode and allows improved control of the catalytic activity through the enzyme's restriction to a specific site. Immobilization at the secondary electrode has the advantage of limiting the reduction of ferricinium which tends to occur in the case of primary electrode immobilization. In certain cases it may be preferable to immobilize the enzyme at some other point than the primary or secondary electrodes.

The immobilization of the enzyme can also increase the efficiency of the electrode thus enabling biosensor detection equipment to be reduced in size.

Preferably enzyme immobilization is achieved using a bovine serum albumin (BSA) linker which avoids direct amino acid attachment to the electrode. This may have the benefit of decreasing enzyme denaturation.

Preferably the enzyme is coupled to BSA through carbohydrate moieties which have previously been oxidised with $NaIO_4$. Carbohydrate attachment has the advantages of immobilizing the enzyme in a manner so as to decrease the risk of restricting substrate diffusion to the active site of the enzyme. Furthermore the large carbohydrate composition of enzymes allows for multiple sites of immobilization which help securing and stabilizing of the enzyme on the electrode. The BSA link has the yet further advantages of creating a protein cushion which protects the enzyme from reductive potentials, providing a buffering microenvironment for the electrode surface electrochemistry (such as pH changes) and preventing the electron transfer agent being reduced directly at the electrode.

Additionally, the electron transfer agent can also be bound to the enzyme, which may be peroxidase, so that there is no need to add separately electron transfer agent to a detection system. This enables a more integrated detection system to be developed by having electrode, enzyme and electron transfer agent bound together. Electron transfer agent immobilization of an amino ferrocene can be achieved by oxidation of a carbohydrate group on the enzyme with sodium periodate and reaction with the amino ferrocene to form a Schiff base. This unstable imine is then reduced with sodium borohydride.

The inventors have found that where detection of cyanide is required the enzyme is preferably horseradish peroxidase (HRP). HRP has the advantage of being a very stable enzyme once immobilized and being commercially available as a very pure preparation.

The overall enzyme reaction of the HRP biosensor can be represented as:

(1)

(2)

(3)

(4)

(5)

Compound 1 is the oxidized form of HRP which is 2 oxidation states above the resting state. The enzyme is reduced to compound 2 and subsequently to the resting state by the electron transfer agent (D(red)).

The electron transfer agent is preferably a metallocene compound. Ideally the electron transfer agent is a ferrocene or ferrocene analogue. Ferrocenes have the advantages of being easily reduced at the secondary electrode and being stable in the reduced form. Furthermore they are not sensitive to light or pH.

A particularly useful feature of ferrocenes is that their structure enables the synthesis of many analogues and ferrocenes therefore can be designed to be electroactive donors towards particular enzymes. Preferred ferrocene derivatives for use with HRP are hydroxymethyl ferrocene, monocarboxylate ferrocene, dimethylaminomethyl ferrocene and 1,1' dicarboxylate ferrocene.

By utilizing a reducing current at the primary electrode for the production of hydrogen peroxide the only source of regenerated ferrocene is through enzymic oxidation which manifests itself in the cathodic secondary electrode current.

Detection and determination can be accomplished by analyzing the inhibition of secondary electrode current by steady state kinetics or by a binding equation.

The pH of the system should be chosen to be within the limits for enzyme activity suitable for the detection method and in the case of HRP is preferably between pH 5 and 8. Ideally the pH is 7 as the enzyme is most stable at this pH.

The operable temperature of the system slay be between 5° and 40° C. but the temperature of the system is preferably towards the middle and upper end of the range as chemical equilibrium is achieved more quickly.

With an aqueous system based on HRP as described herein it is possible to detect under optimum conditions submicromolar (ppb) concentrations of cyanide by the inhibition of ferrocene regeneration current at the secondary electrode.

The typical response time for detection of introduced cyanide is less than 1 second. The rate limiting factor in the detection of cyanide is the diffusion from the gaseous phase into the aqueous phase. Because the binding of cyanide to HRP is a reversible reaction the sensor of the present invention can be repetitively used for the detection of cyanide and because of the inherent stability of sensors made according to the invention it is possible for sensors to be made stable and operable for over six months.

According to a further aspect of the present invention there is provided a biosensor for the detection and determination of concentration of toxins which inhibit enzymic electron transfer activity which comprises:

(i) means for the production of hydrogen peroxide (ii) an enzyme selected from peroxidase, catalase and oxygenase capable of being oxidized by (i);

(iii) an electron transfer agent capable of reducing an oxidized enzyme (ii);

(iv) means for regenerating the electron transfer agent, and (v) means for detecting the change and extent to which the electron transfer agent is regenerated from an oxidized state.

As the biosensor operates in a manner in accordance with the method for detection and determination which utilises substrate regeneration the various embodiments described for that method are applicable in relation to the biosensor itself and consequently do not need to be reiterated in full.

Preferably the enzyme is a peroxidase. Preferably the enzyme is horseradish peroxidase.

Preferably the hydrogen peroxide is produced from solution which contains the enzyme and electron transfer agent. Preferably the solution is aqueous.

The electron transfer agent is preferably a metallocene compound and is ideally a ferrocene or ferrocene analogue.

Preferably the means for production of hydrogen peroxide and the means for regenerating the electron transfer agent are electrodes. The electrode system used maybe a rotating ring-disc electrode (RRDE). Alternatively the electrodes may be of the interdigitated or microband type. An advantage in using interdigitated electrodes is that they have high collection efficiencies. In the case of a RRDE the disc forms the primary electrode and preferably at least the surface is of oxidized carbon. The use of an oxidized carbon electrode enables BSA to be fixed to the electrode by carbodiimide activation. The transport of solution to the electrode is controlled by the rotation rate of the disc with the solution being subsequently transferred from the disc to the secondary ring electrode by the action of disc rotation.

BRIEF DESCRIPTION OF THE DRAWINGS

The invention will now be described by way of example only and with reference to the accompanying Drawings of which.

DESCRIPTION OF THE PREFERRED EMBODIMENTS

Figure 1:
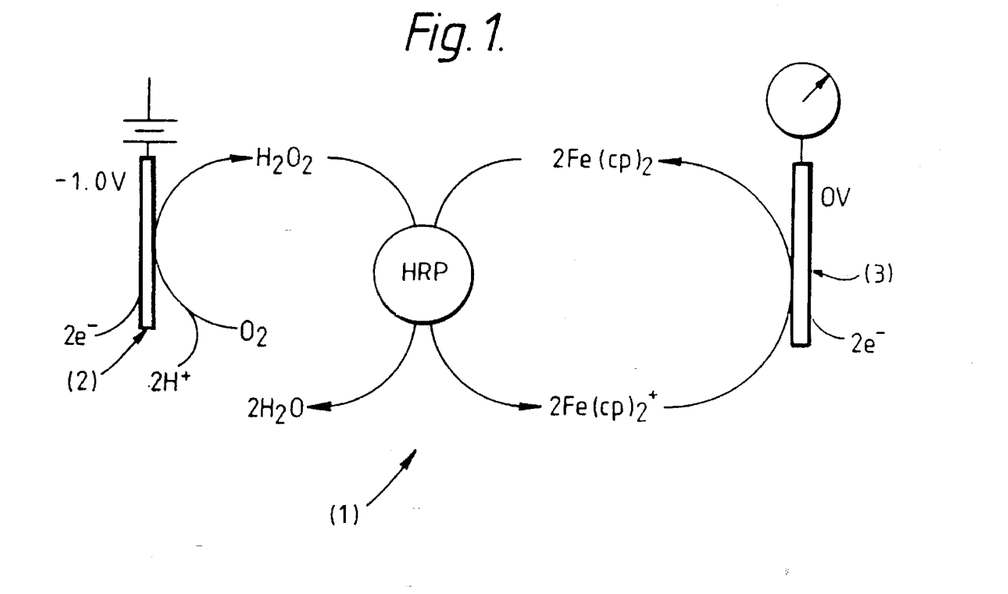
FIG. 1 shows a representation of monitored HRP activity using two working electrodes.
Figure 2:
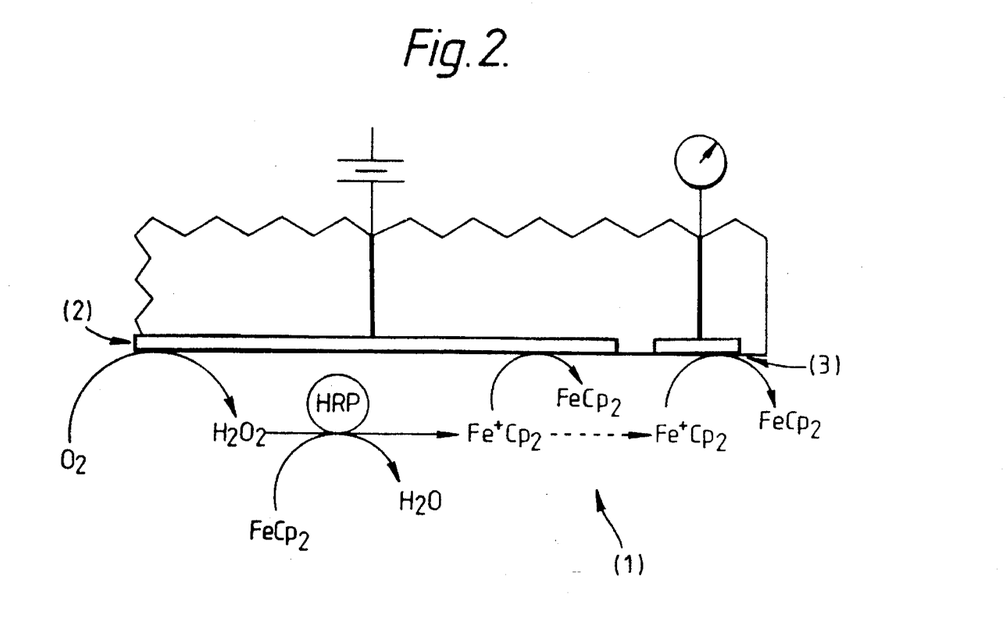
FIG. 2 shows the reactions of FIG. 1 occurring at the surface of a rotating ring disc electrode.

With reference to FIGS. 1 and 2, a dual working electrode system (1) comprises a rotating ring disc electrode (RRDE) of which a rotating disc forms the primary electrode (2) and a ring the secondary electrode (3). The primary electrode (2) is formed as a glassy carbon disc and is sealed in araldite or Kel-F the disc having a diameter of 0.7 cm. The secondary electrode (3) is made as a platinum ring and is also sealed in araldite or Kel-F, having an inner diameter of 0.75 cm and outer diameter of 0.8 cm and being separated from the disc by a 0.05 cm spacer. Both electrodes are polished with a 0.3μ aluminium oxide slurry and subsequently sonicated in a water bath. The remainder of the equipment is described without reference to the figures.

A four electrode analogue potentiostat (not shown) which is optionally computer controlled is used to control the potentials at the working electrodes (2) and (3). The disc electrode (2) is connected to a triangular wave generator (not shown) for potential sweeps and the ring electrode (3) is connected to a constant DC voltage source. The electrode rotation is controlled by a Ursar Scientific rotator. All potentials are quoted with respect to a saturated calomel electrode (SCE) with a 1 $cm^2$ platinum gauze serving as the counter electrode.

The electrodes (2), (3) fit within a electrochemical cell of volume 5–10 mls, the cell being equipped with water jackets for temperature regulation and with the water being supplied from a water bath. The electrodes are positioned so as to minimize solution resistance. In use the collection efficiency was determined experimentally using ferrocene monocarboxylate to be 0.16 which agreed with the predicted value. The purity of horseradish peroxidase (HRP) obtained as highly pure preparations (RZ>3.0) from Biozyme was determined by sodium dodecyl sulfate (SDS) gel electrophoresis. The concentration of enzyme was measured from the absorbance at 403 nm using an extinction coefficient of 90,000M-1 cm-1.

Hydroxymethyl ferrocene obtained from Kodak was made up to the desired concentration on a weight basis. The dissolved oxygen was determined by the Winker method to be 240 μM which agreed with values obtained from a nomegram.

All experiments were carried out at 22° C.

The glassy carbon disc was activated by a combined chemical and electrochemical technique as described by Bourdillon, J. Am. Chem. Soc. 1984, 106, 4701–4706. The disc was held at +2.2V for 30 seconds and during this time the platinum ring was held at −0.2V. The electrode was transferred to a solution of 0.5M $NaKPO_4$, pH 7.0 and the platinum ring was cleaned by cycling between −0.3V and +1.0V for several hours until a stable voltammogram resulted. The disc was then activated with a carbodiimide (0.1M for 1 hr in 0.1M sodium acetate buffer pH 5.0). Following washing with deionized water the electrode was immersed in a solution of bovine serum albumin (BSA, 20 mg/ml in 0.1M sodium acetate, pH 5.0 for 2 hours) obtained from Sigma. Glycoside moieties of HRP were oxidized with $NaIO4$ (8 mM.pH 8.3, 0.1M $NaHCO_3$), 2 hours and the unreacted $NaIO_4$ was removed by adding an excess of ethanediol and passing the protein through a Sephadex G-25 column. The BSA modified electrode was immersed in an oxidized peroxidase solution and slowly rotated for 2 hours in a sodium bicarbonate buffer (0.1M at pH 9.0). The resulting imine bond linking BSA to HRP was reduced with $NaBH_4$ (100 ml of 5 mg/ml for 1 hour and repeated once). The electrode was rotated in 0.1M $NaKPO_4$ and the ring cycled between −0.3V and +1.0V for 2 hours to help remove any loosely absorbed protein.

The enzyme modified electrode was analyzed for peroxidase activity by a colorimetric method. The electrode was immersed in an assay mixture and rotated at a speed which overcame any diffusion limitations (>20 rpm). Absorbance changes were monitored by means of a spectrophotometer at a single wavelength. The actual enzyme activity was then determined from a standard curve. In this way, the electrodes were checked for activity rather than for the amount of protein that was immobilized. The amount of enzyme immobilized based on its activity was approximately $2\times10^{-13}$ mol cm$^2$, which is similar to concentrations achieved through other immobilization procedures.

The electrocatalytic activity of HRP as shown in FIGS. 1 and 2 was typically assessed by immersing the rotating ring disc electrode in a buffered solution containing peroxidase and hydroxymethyl ferrocene mediator. The electrode was rotated at a constant speed to control the transport of material to the disc electrode and subsequently out to the ring. A cathodic potential sweep was applied to the glassy carbon disc at 0.1V/S. The platinum ring was held at constant potential of 0V and the current at the ring as a function of the disc potential was measured. Before determination of the peroxidase generated ring current, following electrode immersion, the ring current (background current) was allowed to stabilize (about 5 min). A cathodic ring current resulting from the reduction of enzymically oxidized mediator was then measured at disc potentials which resulted in the partial reduction of molecular oxygen. The catalytic current was defined as the net reductive current occurring at a disc potential of 0 volts.

The actual profile of the reduction current seen at the ring electrode is a function of the concentrations of the enzyme and substrates, as well as the rotation rate of the electrode, the sweep rate at the disc and the potential of the ring. The magnitude of this current also depends on the fraction of enzymatically generated ferricinium (oxidized ferrocene) which actually reaches the ring.

Figure 3:
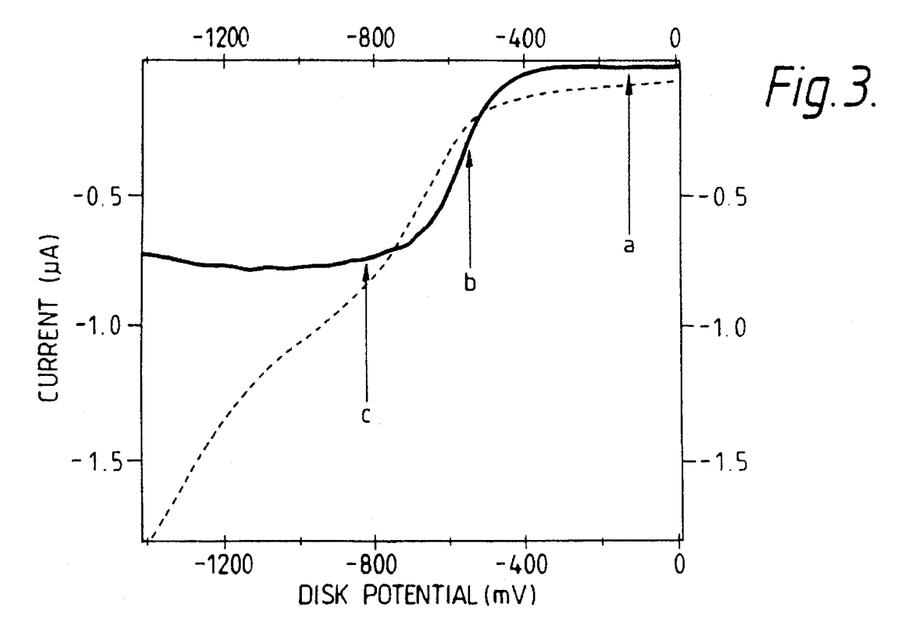
FIG. 3 shows a graph of the currents resulting at the primary and secondary electrodes of the ring disc electrode with the ring held at 0V, a scan speed of 0.1V/s, electrode (disc) rotation rate of 4 cps and in the presence of hydroxymethyl ferrocene 0.3 mM, HRP 1.25 uM, KCl 0.1M, and buffer $KHPO_4$ 0.05M at pH 7.

A trace depicting ring current as a function of disc potential is shown in FIG. 3. The continuous line is indicative of ferrocene reduction at the ring while the dotted line indicates oxygen reduction at the disc (x10$^{-2}$). Distinct regions of faradic activity result at the ring as the disc becomes more cathodic. Initially the horizontal nature of the trace (a) indicates that there is no ferrocene mediated electroactivity at the ring. At potentials more negative than −0.3V (b) there is an increase in cathodic ring current as the disc becomes more reducing. This increase is directly proportional to the production of hydrogen peroxide at the disc. As the rate of peroxide generation increases the magnitude of the ring current becomes controlled by the reaction rate of the enzyme. Thus in region (c) the enzyme kinetics dominate the current profile with the current produced by regeneration of ferrocene from ferricinium being dominated by HRP enzyme kinetics.

Several ferrocenes shown in Table 1 were tested for their ability to act as mediators for HRP reduction. The ring current as a function of ferrocene structure and redox potential is demonstrated with HRP 2.5 µM and currents taken at a disc potential of −1.2V. In Table 1 $Ep_{1/2}$ is the redox potential and demonstrates that there is no relationship between the current produced and the redox potential and therefore that ferrocene reducing agents should not be chosen as mediators just because they are easily oxidized.

TABLE 1

| Ferrocene Derivative (0.5 mM) | $Ep_{1/2}$ (mv) | Current (mA) | Relative Current |
| --- | --- | --- | --- |
| Hydroxymethyl Ferrocene | 210 | 3.8 | 100% |
| Monocarboxylate Ferrocene | 295 | 0.64 | 17% |
| Dimethylaminomethyl Ferrocene | 490 | 0.22 | 6% |

TABLE 1-continued

| Ferrocene Derivative (0.5 mM) | $Ep_{1/2}$ (mv) | Current (mA) | Relative Current |
| --- | --- | --- | --- |
| 1,1' Dicarboxylate Ferrocene | 420 | 0.10 | 3% |

Spectrophotometric assays measuring the rate of ferrocene oxidation were carried out with HRP, hydroxymethyl ferrocene, hydrogen peroxide and buffer, the rate of change in absorbance was monitored at 330 nm using a Philips PU 8720 spectrophotometer.

Determination of the effect of rotation rate on ring current revealed that ring current decreased with increasing rotation rate. Under the conditions described in FIG. 4 the maximum current was achieved at a rotation rate of 2 cps. Ring currents at rotation rates of less than 2 cps were complicated by a decrease in collection efficiency.

Figure 4:
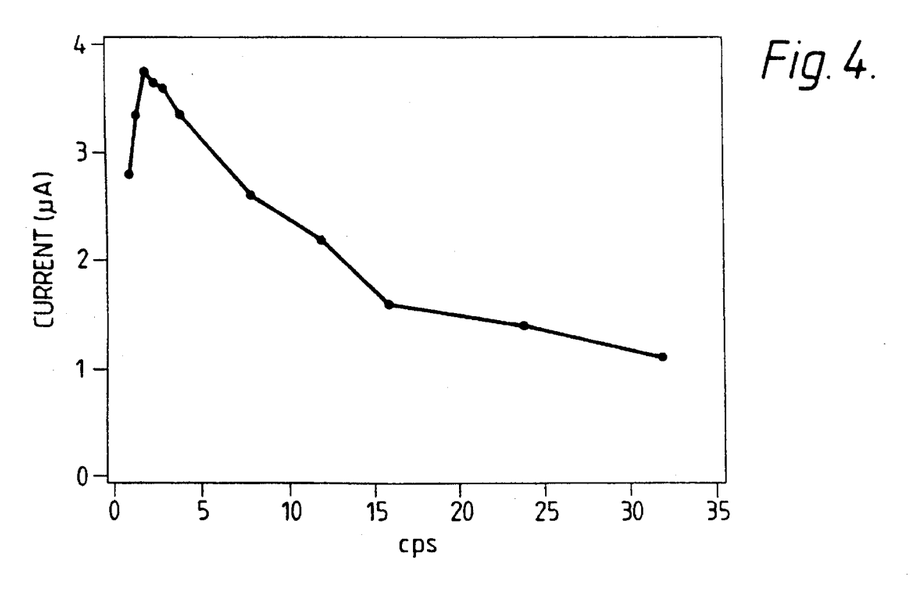
FIG. 4 shows the effect of primary (disc) electrode rotation rate on the secondary (ring) electrode current in the presence of hydroxymethyl ferrocene 1 mM, HRP 2.5 uM and at a disc potential of −1.2V during a disc potential sweep of 0.1V/s.

Currents also decreased because of the increasing dominance of oxygen reduction limited kinetics. As a result most experiments were performed at a rotation rate of 4 cps which gave a good flux of ferricinium to the ring and a sufficient transit time for enzyme reaction in solution.

Figure 5:
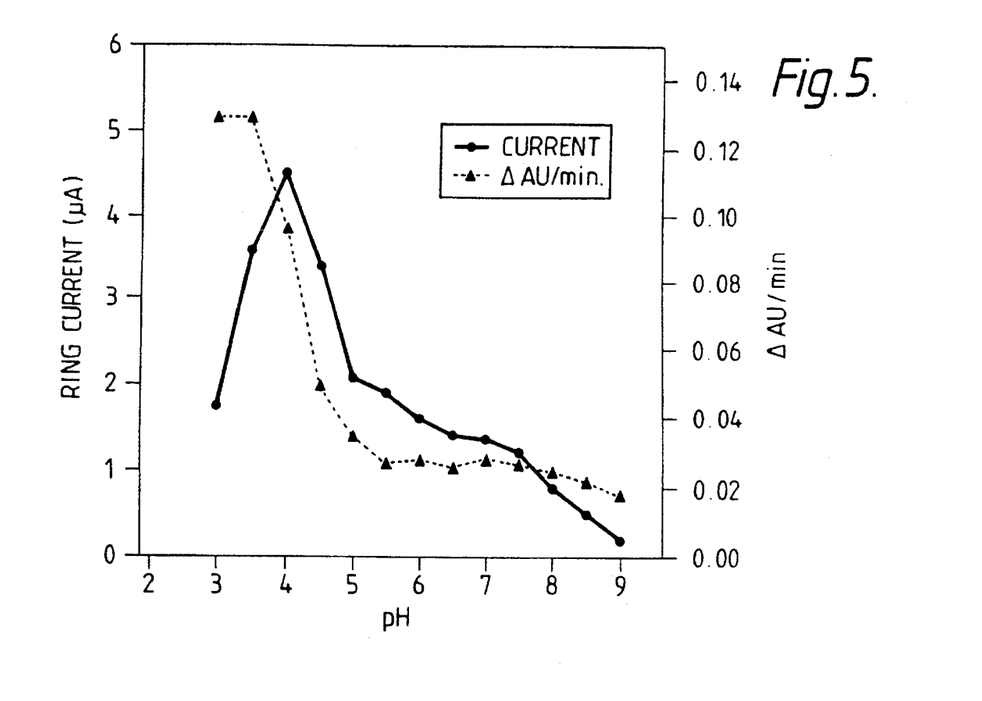
FIG. 5 shows the measurement of enzymatic oxidation of ferrocene by amperometric means and by spectrophotometric means. For amperometric analysis there was HRP 1.25 uM, hydroxymethyl ferrocene 0.3 mM, the spectrophotometric assay was undertaken with HRP 1.25 uM, hydroxymethyl ferrocene 0.5 mM, $H_2O_2$ 10 mM. Buffers used: pH 3–5.5 acetate, pH 5–7.5 potassium phosphate, pH 7–9 Tris, all at 50 mM.

FIG. 5 shows the effect of pH on ring current with maximal response being achieved at pH 4.0. However a pH of 7.0 was chosen as being convenient because the ring current showed little fluctuation and the enzyme stability was improved.

The inhibitory effect of cyanide on HRP generated ring current was measured under steady state conditions. Cyanide was added from stock solution to the electrochemical system and binding was allowed to reach equilibrium (about 30 sec). The ring current generated under conditions of substrate oxidation limited kinetics was determined by cycling the disc between 0 and −1.2V. The net ring current resulting from the catalytic activity of HRP in the region of $H_2O_2$ production was determined by subtracting the ring current occurring at 0V. Thus, the ring current is a direct measure of the ability of HRP to oxidize ferrocene.

Figure 6:
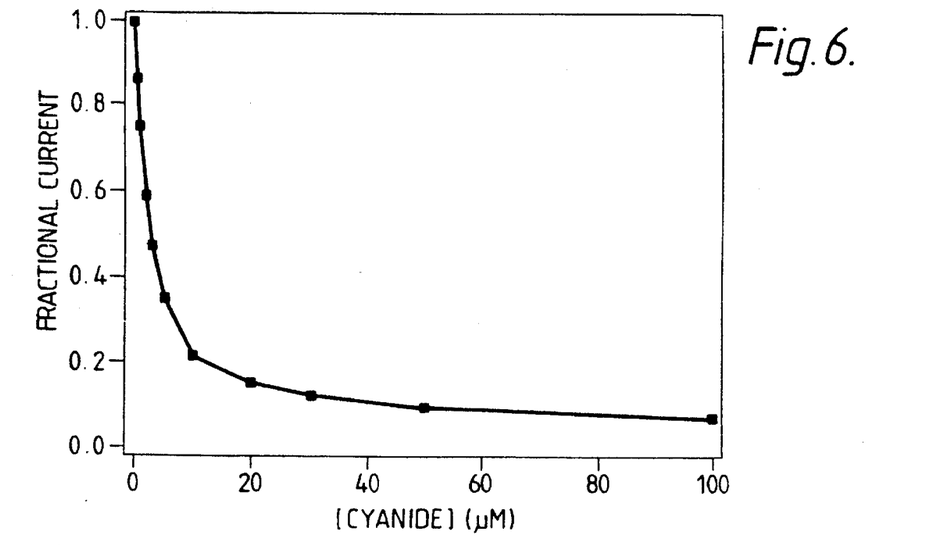
FIG. 6 shows the fractional ring current remaining following the introduction of potassium cyanide. Hydroxymethyl ferrocene 0.3 mM, HRP 2.5 uM at a disc potential of −1.2V disc sweep of 0.1 V/s and ring at 0V. The current was measured after 1 minute equilibration following the addition of cyanide.

FIG. 6 shows the effect that cyanide had on the catalytic ring current. The inhibition of ring current can be standardized by expressing it as a percent inhibition of total current. These results can be analyzed in the first instance using a binding equation. If it is assumed that cyanide binds with HRP on a one to one basis and that the complex formation is directly proportional to the inhibition of current then:

$$\% \text{ Inhibition} = \frac{1}{Imax} = \frac{[HRP-CN]}{[HRP]_T} = \frac{[CN]}{[CN]+K_1}$$

where [CN] is the free inhibitor concentration (=$[CN]_T$−[HRP−CN], $[CN]_T$ is the total cyanide added), and [HRP−CN]=$[HRP]_T\times$(% inhibition).

Figure 7:
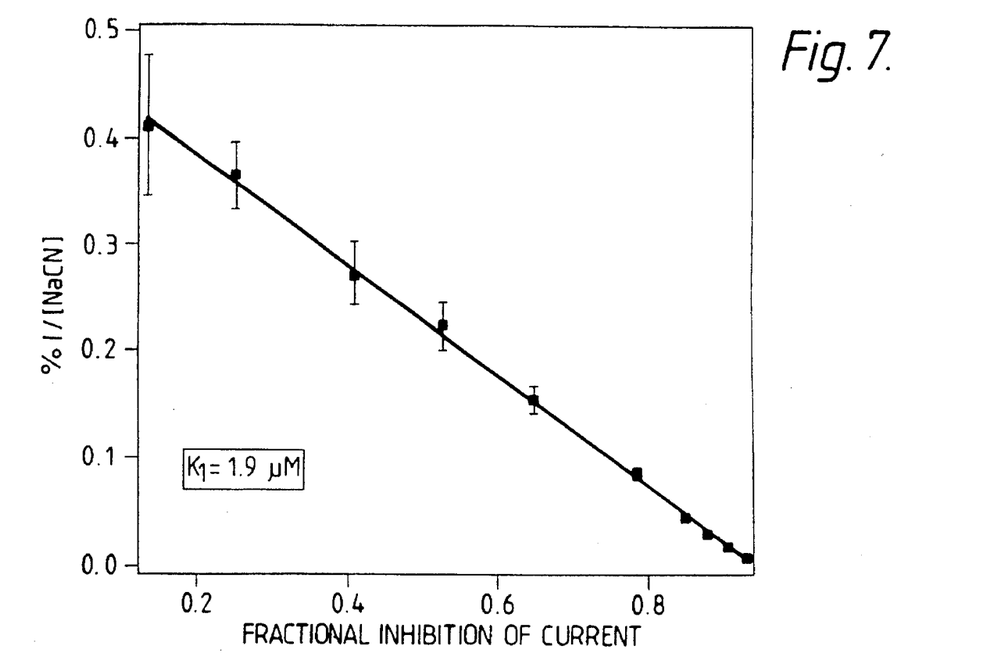
FIG. 7 shows a Scatchcard analysis of the data shown in FIG. 4 using the equation: % I/[CN]=−% I/$K_1$+$I_{max}$/$K_1$. Points represent the means of 5 determinations+the standard deviation. The $K_1$ represents the free concentration of cyanide required for 50% inhibition.

FIG. 7 shows a Scatchcard analysis of a typical set of data. $K_1$ is the apparent inhibition constant for cyanide. From inhibition curves the $K_1$ was calculated by both linear and non-linear regression methods to be about 2 uM. This concentration corresponds to $52\times10^{-6}$ mg/ml or 52 ppb.

Figure 8:
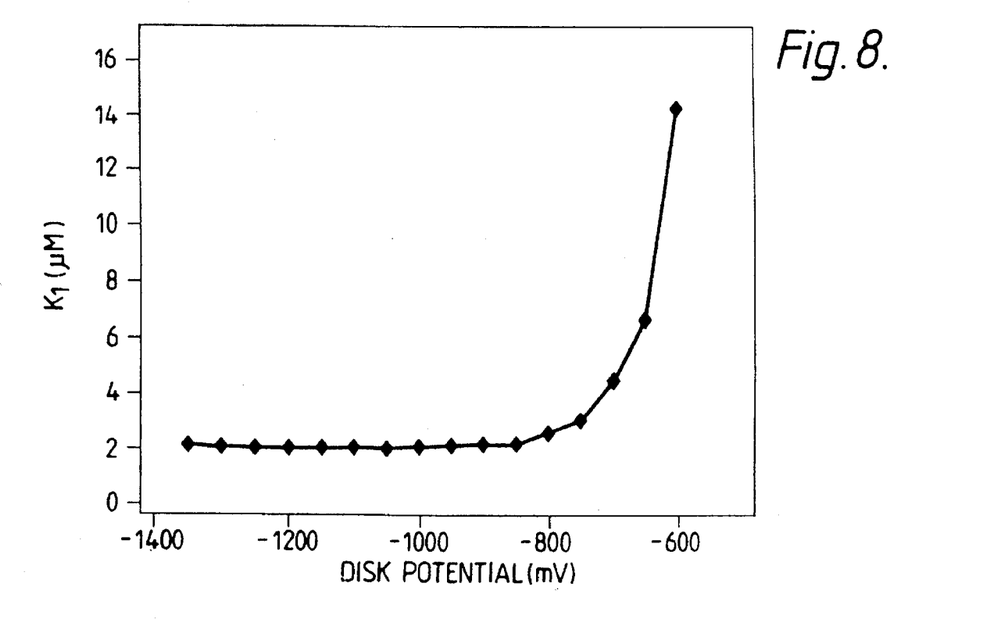
FIG. 8 shows the inhibition constant for cyanide determined at different rates of $H_2O_2$ production as determined by the disc potential HRP 1.25 uM, hydroxymethl ferrocene 0.3 mM.

FIG. 8 displays the apparent $K_1$ values for cyanide as a function of disc potential. As the disc potential becomes more negative, the $K_1$ for cyanide decreases. Under condition of low hydrogen peroxide production the ring current is proportional to the disc current and an excess of enzyme exists. Thus the ring current is determined by the peroxide produced and current inhibition is not proportional to enzyme inhibition. Below a disc potential of −0.8V the inhibition of HRP by cyanide reaches a maximal efficiency.

The modified electrode was found to remain stable for more than 6 months when stored in 1M phosphate buffer at pH7.

Figure 9:
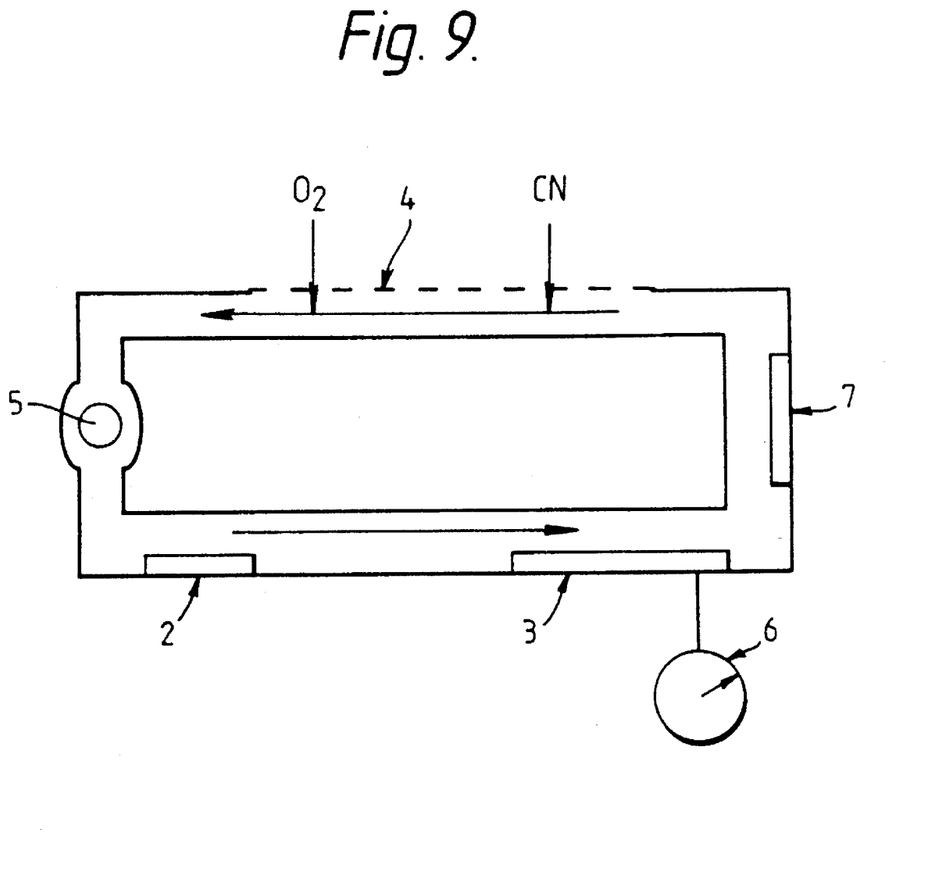
FIG. 9 shows a closed loop cyanide sensor.

FIG. 9 shows a version of a closed loop cyanide sensor. The oxygen necessary for production of hydrogen peroxide and cyanide enter the sensor through a gas permeable membrane (4) of large surface area. These gases dissolve in solution and a pump (5) is used to transfer them between the primary (2) and secondary (3) electrodes on a continuous basis as shown by the arrows. The primary electrode which has HRP bound to it (not shown) generates hydrogen peroxide. The secondary electrode detects ferricinium which has been oxidized from ferrocene by oxidized HRP, the HRP having been oxidized by the hydrogen peroxide. A meter (6) gives the extent of conversion of ferrocene to ferricinium through the current passed in reduction back to ferrocene. A further electrode (7) scavenges for unreacted peroxide or unreduced ferricinium etc. The electrode is positioned downstream of the primary and secondary electrodes but before the gas permeable membrane. This self contained system which is open to environmental gases can detect by inhibition of HRP enzymic activity the presence and concentration of cyanide or similar inhibitory gases.

Detection apparatus produced in accordance with the invention has the capability for continuous monitoring.

We claim:

1. A method of detecting and determining the concentration of a compound which inhibits electron transfer activity of an enzyme, said method comprising the steps of:

(a) providing in an aqueous environment an enzyme selected from the group consisting of peroxidase, catalase and oxygenase whose electron transfer activity is inhibited when bound to the compound;

(b) providing hydrogen peroxide in the environment to oxidize the enzyme;

(c) reducing the oxidized enzyme with an electron transfer agent wherein the electron transfer agent is oxidized as the oxidized enzyme is reduced; and (d) detecting the concentration of the compound by measuring the change in and extent to which the electron transfer agent is regenerated from its oxidized state.

2. The method as claimed in claim 1 wherein the enzyme is a peroxidase.

3. The method as claimed in claim 1 wherein the aqueous environment is buffered.

4. The method as claimed in claim 1 wherein the aqueous environment has oxygen dissolved within it, the method further including the step of reducing the oxygen to hydrogen peroxide at a primary electrode while regenerating the electron transfer agent at a secondary electrode.

5. The method as claimed in claim 4 wherein the enzyme is immobilized at the primary electrode.

6. The method as claimed in claim 5 wherein the enzyme is immobilized with a bovine serum albumin linker.

7. The method as claimed in claim 6 wherein the enzyme is coupled to bovine serum albumin through carbohydrate moieties previously oxidized with $NaIO_4$.

8. The method as claimed in claim 1 wherein the enzyme used is immobilized.

9. The method as claimed in claim 1 wherein the enzyme is horseradish peroxidase.

10. The method as claimed in claim 9 wherein the method is conducted in an aqueous environment at a pH value between 5 and 8.

11. The method as claimed in claim 10 wherein the pH value is 7.

12. The method as claimed in claim 1 wherein the compound is cyanide.

13. The method as claimed in claim 1 wherein the electron transfer agent is a metallocene compound.

14. The method as claimed in claim 13 wherein the electron transfer agent is a ferrocene or ferrocene analogue.

15. The method as claimed in claim 14 wherein the electron transfer agent is selected from the group consisting of hydroxymethyl ferrocene, monocarboxylate ferrocene, dimethylaminomethyl ferrocene and 1,1' dicarboxylate ferrocene.

16. The method as claimed in claim 15 wherein the electron transfer agent is hydroxymethyl ferrocene.

17. The method as claimed in claim 1 wherein the method is conducted at a temperature of between 5° and 40° C.

* * * * *